United States Patent
Fischer

(10) Patent No.: US 9,470,513 B2
(45) Date of Patent: Oct. 18, 2016

(54) APPARATUS AND METHOD FOR DETERMINING AT LEAST ONE PARAMETER OF A PRODUCED SAUSAGE

(71) Applicant: ALBERT HANDTMANN MASCHINENFABRIK GMBH & CO. KG, Biberach (DE)

(72) Inventor: Thomas Fischer, Gutenzell (DE)

(73) Assignee: ALBERT HANDTMANN MASCHINENFABRIK GMBH & CO. KG, Biberach (DE)

( * ) Notice: Subject to any disclaimer, the term of this patent is extended or adjusted under 35 U.S.C. 154(b) by 261 days.

(21) Appl. No.: 14/223,736

(22) Filed: Mar. 24, 2014

(65) Prior Publication Data

US 2014/0333938 A1  Nov. 13, 2014

(30) Foreign Application Priority Data

May 10, 2013 (EP) .................................. 13167225

(51) Int. Cl.
  *G01B 11/24* (2006.01)
  *G01B 11/255* (2006.01)
  *A22C 11/00* (2006.01)
  *A22C 11/02* (2006.01)
  *A22C 17/00* (2006.01)
  *G01N 33/12* (2006.01)

(52) U.S. Cl.
  CPC .............. *G01B 11/24* (2013.01); *A22C 11/00* (2013.01); *A22C 11/0245* (2013.01); *A22C 17/0073* (2013.01); *G01B 11/255* (2013.01); *G01N 33/12* (2013.01)

(58) Field of Classification Search
  None
  See application file for complete search history.

(56) References Cited

U.S. PATENT DOCUMENTS

| 4,434,529 A | 3/1984 | Jensen |
| 4,766,645 A | 8/1988 | Lamartino et al. |
| 5,421,137 A * | 6/1995 | Stimpfl .............. A22C 11/006 53/236 |
| 2007/0052978 A1 * | 3/2007 | Pingel .................. G01B 11/06 356/632 |

FOREIGN PATENT DOCUMENTS

| DE | 4307637 A1 | 12/1993 |
| EP | 1570740 A1 | 9/2005 |
| EP | 1623628 A2 | 2/2006 |
| EP | 2084969 A2 | 8/2009 |
| JP | 58-078534 | 10/1982 |
| JP | 63283534 | 4/1987 |
| JP | 2004033218 A | 2/2004 |

(Continued)

OTHER PUBLICATIONS

European Search Report for EP 13167225, dated Sep. 30, 2013.

(Continued)

*Primary Examiner* — Kara E Geisel
*Assistant Examiner* — Amanda Merlino
(74) *Attorney, Agent, or Firm* — Marshall, Gerstein & Borun LLP

(57) ABSTRACT

An apparatus and a method for determining at least one parameter relating to the shape of the sausage, which is transported on a transport device, in particular between two circulating means of transport. A measuring device has at least one distance sensor, which is disposed in such a way that said sensor can detect a distance c to a sausage that is being transported. Furthermore, an evaluation device is provided, which determines at least one parameter relating to the sausage as a function of the distance.

24 Claims, 5 Drawing Sheets

(56) References Cited

FOREIGN PATENT DOCUMENTS

| | | | |
|---|---|---|---|
| JP | 2004524008 | A | 8/2004 |
| JP | 2008175691 | A | 7/2008 |
| JP | 2008189821 | A | 8/2008 |
| JP | 2010286409 | A | 12/2010 |
| JP | 2011194021 | A | 10/2011 |

OTHER PUBLICATIONS

First Office Action for application No. P2014-054895, Japanese Patent Office, dated Mar. 24, 2015.

Office Action for Application No. P2014-054895, dated Nov. 4, 2015.

* cited by examiner

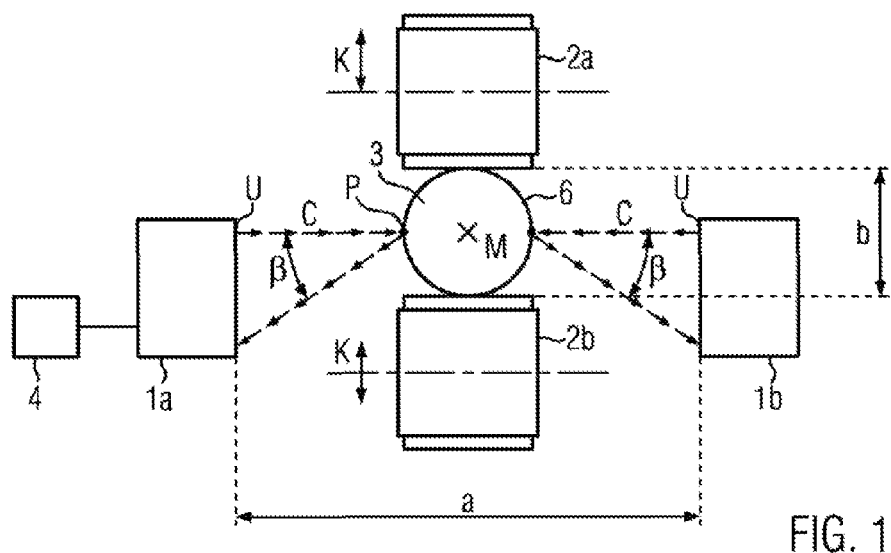
FIG. 1
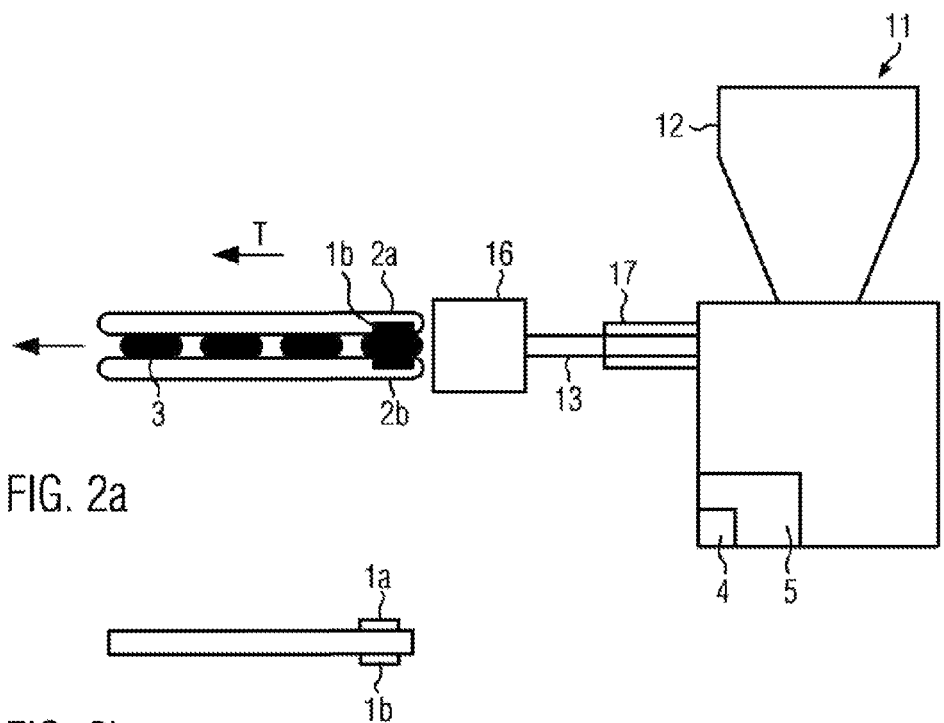
FIG. 2a
FIG. 2b

APPARATUS AND METHOD FOR DETERMINING AT LEAST ONE PARAMETER OF A PRODUCED SAUSAGE

CROSS-REFERENCE TO RELATED APPLICATION

The application claims priority of European Application No. 13 167 225.5, filed May 10, 2013. The priority application, EPO 13 167 225.5, is hereby incorporated by reference.

FIELD OF THE DISCLOSURE

The disclosure relates to an apparatus and a method for determining at least one parameter relating to the shape of the sausage.

BACKGROUND

Various apparatuses and methods for detecting the shape of filled sausages are already known.

Thus, for example, it is generally known, sausages that are transported on a conveyor belt can be optically detected using cameras in the reflected light method or transmitted light method.

Disadvantages in the detection of parameters that relate to the shape of the sausage are, for example:
Elaborate, sensitive and expensive equipment,
A great deal of space required in the system. The shape of sausages, which are being transported between two conveyor belts for example, cannot be detected:
Interference from stray light,
Recognition rate is limited,
Elaborate and difficult programming and teaching the target size and threshold of tolerance (good/bad parts).

DE 4307637 describes a method for detecting the length of a sausage, so that the sausages can be separated from one another. The start of the sausage and the end of the sausage, and therefore the length, can be detected by means of a light beam or light curtain. The disadvantage to this method is that no additional parameters such as curvature can be detected when the sausages are held between two conveyor belts.

SUMMARY

Proceeding from this, the object of the present disclosure is to provide an improved apparatus and an improved method, which make it possible to detect parameters relating to the shape of a produced sausage in a simple manner.

The apparatus according to the disclosure is suitable for determining at least one parameter of a produced sausage, i.e. a parameter relating to the shape of a sausage. A transport device is thereby provided, in particular two circulating means of transport such as conveyor belts, for example. The produced sausage in the form of individual sausages or strings of sausages of a certain number can thereby be transported on the means of transport.

According to the disclosure, the apparatus has a distance sensor, which is disposed in such a way that said sensor can detect a distance to the sausage. Furthermore, an evaluation device is provided, which determines at least one parameter relating to the sausage as a function of the distance. Using the distance sensor, the surface of the sausage passing by the sensor can be scanned, whereby a plurality of parameters relating to the shape of the sausage can be determined in a simple manner. When the at least one distance sensor is laterally disposed with respect to the means of transport, for example, these parameters can also be determined for sausages, which are being conveyed between circulating means of transport such as conveyor belts, for example. The apparatus of the present disclosure is thus particularly advantageous for detecting the parameters of sausages that are held between two means of transport. The apparatus is also suitable for sausages that are lying on and being conveyed on a conveyor belt, however.

The apparatus preferably comprises an evaluation device, which is designed in such a way that a signal is generated as a function of the at least one detected parameter, in order to transport the sausage for corresponding further processing steps depending upon this signal. Such processing steps may include a step, for example, in which sausages having deviating parameters are automatically discharged from further processing, for example in the case of split casings, a length or caliber that falls outside of the tolerances, a failed cutting function, etc. Depending on certain parameters, the sausages may also be transferred into groups of sausages having appropriate, differing parameters and if applicable, further processed in a different manner.

In the present apparatus and method of the disclosure, it is advantageous that a plurality of parameters can be detected by means of the at least one distance sensor. A least one of the following parameters is thereby determined:

Portion length, caliber, direction of curvature, size of curvature, split casing, presence of a separation point between successive sausage portions.

When determining the portion length, the evaluation unit may then determine whether the length falls within certain specifications or a certain tolerances for example, in particular in the case of portions having less curvature. In determining the caliber, it is possible to determine whether the casing is underfilled over overfilled. When determining the direction of curvature, it is possible to determine whether the sausages are lying with the curvature facing to the left or to the right on the means of transport. These parameters can then be used, for example to form groups of sausages having the same orientation. This is important for placing these precisely in a tray. If the size of curvature is determined, the extended length can be calculated therefrom, for example. In the case of deviations, for example, a sausage may be discarded from production, for example. Furthermore, it is possible to determine whether consecutive sausage portions have been cut or not. Here again, the corresponding sausage or sausages may be discharged, for example when a separation point is missing. Likewise, a corresponding sausage may be discharged if a parameter is determined for whether a split casing exists. The at least one distance sensor is thereby preferably a reflex scanner, in particular a laser distance sensor. The measurement is thereby preferably taken with the help of laser triangulation or by means of travel time measurement or phase position measurement. Distance measurement with the help of other optical sensors such as infrared sensors is also possible, however. Appropriate measurement methods are simple and cost-effective, and require little space.

It is especially advantageous when the measuring device comprises the distance sensors, which are disposed on opposite sides of the transport device at defined locations, in particular on opposite sides of the circulating means of transport. Since the distance sensors are disposed at defined locations, and therefore the distance between them is known, a plurality of parameters can be precisely determined.

It is advantageous when the at least one distance sensor is thereby disposed at a height such that a measuring point P lies on a plane, which is at the same distance from each of the two circulating means of transport. It is thus ensured that the precise caliber across a sausage can be determined. Furthermore, it is also ensured that the laser beam for determining a separation point is directed at the twist in the casing located between two sausages when the sausages are not separated from one another.

The distance of the two circulating means of transport from one another may be advantageously adjusted in such a way that sausages having a different caliber can also be produced, and the parameters thereof determined. However it is advantageous that, when the means of transport are moved towards one another or away from one another, for example, the midpoint between the means of transport remains constant, in such a way that a precise measurement of the different parameters is possible without having to relocated the corresponding sensors. This simplifies the method.

It is also possible to dispose a plurality of distance sensors in one direction, one above the other, wherein this direction extends perpendicular to a direction of transport T of the sausages. This is especially advantageous when natural casings are being processed, in which the twist between two individual sausages is not always located exactly in the region of the center axis. Furthermore, in addition to the measuring device, a line sensor can be disposed, which is oriented perpendicular to the direction of transport. A section point that deviates from the center axis can thereby be located by means of this line sensor.

In the case of the method for determining at least one parameter relating to the shape of the sausage, the produced sausage is transported on a transport device, in particular between two circulating means of transport, and in so doing, detects the distance from a defined location to the sausage, and determines at least one parameter relating to the sausage as a function of the distance.

It is advantageous that, according to the present disclosure, a plurality of parameters relating to the shape of the sausage can be determined by only one apparatus, and said parameters can be used for further processing steps. Depending on specified tolerances, the individual sausages or a specific number of connected sausages can be fed to the desired processing steps.

It is especially advantageous when the distance of two sides that are opposite one another with respect to the means of transport are measured, and the at least one parameter is determined or calculated as a function of the two distances. Thus an even greater number of parameters can be precisely determined, when the at least one determined parameter is compared to a target parameter or range of target parameters and the sausage can be transported to a corresponding further processing step depending on the comparison.

The distance is advantageously determined as a function of the time or of the distance traveled by the transport device. Thus, for example, a corresponding parameter can be calculated with the help of a measured value of the distance sensor or the distance sensors respectively, and transducers of the transport device.

The length of the sausage, for example, can be determined as a parameter from the rising and falling signal edge of a distance signal and the distance therebetween traveled by the transport device, in particular the number of increments on the drive on a means of transport.

The direction of curvature of the sausage lying on the transport device can be determined in a simple manner by means of the direction of curvature of the distance signal. According to a preferred embodiment, the distance signal is thereby determined as a function of the time or the distance from the opposite side of the transport device to the sausage, wherein the case of curved sausages, the characteristic of the distance signal on the opposite side is reversed, and the direction of curvature is determined from the distance signals of the opposite sides. Since in the case of a curved sausage, the total of each of the signals at a point in time is constant, $S_1+S_2$=Const, on the opposite sides, the direction of curvature can be determined, for example by subtracting the two measured values by determining whether the result is positive or negative.

When the sausage caliber is determined as a parameter, the distance to the sausage from two distance sensors disposed opposite one another in reference to the means of transport at defined locations is measured, wherein the distance of the sensors minus the two measured distances to the sausage yields the caliber of a curved sausage in the center of the sausage, wherein the caliber is preferably determined at a plurality of locations of the sausage, preferably at each location of the sausage. Thus it is not only possible to determine the sausage caliber itself, but it is also possible to determine whether the sausage across the length of the sausage is constant or falls in a specific target range.

In the case of curved sausages, the determined caliber is corrected as a function of the curvature.

The size of the curvature may also be determined as a parameter. The size of curvature can be obtained by subtracting the smallest measured distance signal from the largest measured distance signal.

The actual length of the extended sausage can be determined from the parameter of the size of curvature and the length of the curved sausage.

According to the present disclosure, it is possible to determine that a separation point between successive sausages exists, when the distance signal drops to zero and in particular, when the distance signal drops to zero or falls below a specific threshold value for a predetermined period of time or transport distance, and in particular, when the distance signal remains below a specific threshold value for a predetermined period of time or transport distance. If two consecutive individual sausages are cut, there is no reflection signal at this location, so that it is possible to determine in a simple manner whether the sausages were cut. It is also possible, however, that the distance signal does not drop entirely to zero due to a very a distance between the sausages, or due to meat fibers located between the sausages, or even signal noise. A specific threshold value can then be determined through experimentation, which serves as the basis for evaluating a separation point. In so going, it is also possible to determine the distance between two consecutive sausages.

A split casing may also be determined as a parameter, for example when no sinking signal edge of the distance signal occurs after a rising signal edge after a specific period of time.

It is advantageous that the direction of curvature of the sausages transported by means of the transport device can be determined, and then groups of sausages having the same direction of curvature can be formed. Depending on the direction of curvature, the sausage may be transported on different, additional transport devices, for example, and/or may be placed in different receptacles. The sausages are sorted according to their curvature is essential for the precise placement of the sausages in trays.

BRIEF DESCRIPTION OF THE SEVERAL
VIEWS OF THE DRAWINGS

The invention is described in greater detail in conjunction with the following Figures.

FIG. 1 shows a rough schematic representation of a first embodiment according to the present disclosure.

FIG. 2a shows a rough schematic representation of a side view of a filling machine having an apparatus according to the present disclosure.

FIG. 2b shows a top view of the apparatus according to the present disclosure shown in FIG. 2a.

DETAILED DESCRIPT OF THE PREFERRED EMBODIMENTS

Figure 3:
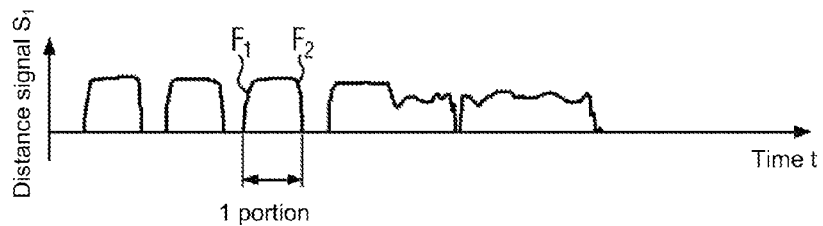
FIG. 3 shows a schematic representation of a distance signal as a function of the time for the recognition of the length.

FIG. 1 shows a preferred embodiment according to the present disclosure. The apparatus according to the disclosure is integrated into a filling machine 11 for producing sausages, for example, as shown in FIG. 2a. A filling machine 11 thereby comprises a hopper 12 to accommodate a pasty mass, as well as an integrated conveyor (not shown here), by means of which the pasty mass can be ejected into a sausage casing by means of a filling tube 13. A twist-off point can be produced for separating sausages, for example by means of a twist-off device 17. A separation device having separating elements can be provided after the filling tube in the direction of transport T, as is schematically depicted by 16, said separating elements acts on the filled string of sausage in and displaces the pasty mass in order to create a separation point. In addition, a cutting device may also be provided here, which cuts the separated individual sausages into single sausages or groups of sausages having a number of single sausages. The produced sausages are further transported in the direction of transport T by means of a transport device 2a,b. Here, the transport device comprises two circulating means of transport, for example two circulating conveyor belts, between which the sausages 3 are held. The means of transport 2a,b may be disposed vertically or horizontally. In order to be able to detect parameters with reference to the shape of the sausages, the apparatus comprises at least one distance sensor 1a,b, as is apparent from FIGS. 2a and 2b as well as FIG. 1; in this embodiment, for example, there are two distance sensors 1a,b located opposite one another. As is apparent, in particular from FIG. 1, the two distance sensors 1a, 1b are at a predefined distance a and are disposed at predetermined locations. The distance sensors 1a, 1b are preferably disposed in such a way that a measuring point P lies on a plane, which is at the same distance from each of the two means of transport 2a, 2b, in such a way that the precise diameter that passes through the center axis M of the sausage 3 can be detected, for example.

A reflex scanner is preferably used as a distance sensor. In this embodiment, a laser distance sensor 1a, 1b is used, which functions according to the triangulation principle. In the case of laser triangulation, a laser beam and if applicable, the beam from a light diode, is focused on a measuring point P on the passing sausage, and is observed using an adjacent detector located in the sensor, for example a camera, a position-sensitive photodiode or a CCD sensor. If the distance of the sausage from the sensor changes, the angle β at which the light is reflected also changes and therefore the position on the photo detector. The distance of the surface of the sausage from the sensor is calculated from the position of the received reflected beam. Thus the sensors 1a,b can scan the surface of the passing sausage. The distance sensors 1a,b then channel a distance signal corresponding to the distance c to an evaluation device 4. The evaluation device 4 may be disposed in the controller 5 of the filling machine 11 for example, however it may also be provided in a separate control step or calculation step. Instead of the laser distance sensor, another optic sensor could be used to measure distance for example, such as an infrared sensor.

Figure 11:
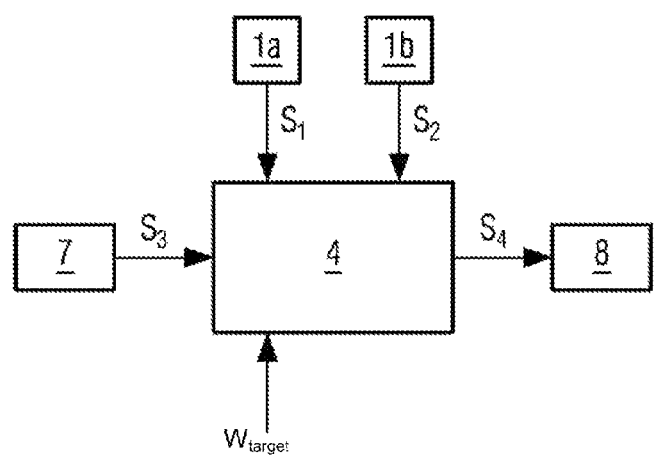
FIG. 11 shows a rough schematic representation of a circuit diagram according to the present disclosure.

As is particularly evident from FIG. 11, the distance measurement signals S1 and S2 can be fed back to the evaluation unit 4. Furthermore, the evaluation unit 4 may also receive additional signals, for example from a transducer 7 of the transport device 2a,b, wherein the signal S3 corresponds to the distance traveled by the transport device 2a,b per unit of time. The corresponding signal S3 may also be supplied by the control unit 5. As explained in greater detail below, the evaluation device can detect or calculate a corresponding parameter relating to the sausage as a function of the distance c the two distances c on opposite sides of the transport device, wherein a signal S4 is generated as a function of the at least one detected parameter, which is forwarded to a device 8 in order to transport the sausage for corresponding further processing steps depending on this signal. The device 8 may be slide feed for example, which pushes the sausages onto different conveyor belts or discharges sausages from further processing. Corresponding target values $W_{target}$ or ranges of target values may also be entered into the evaluation device 4, to which values the determined parameters may be compared by means of a comparator not separately shown. A decision is then made concerning further processing on the basis of this comparison.

As is further evident from FIG. 1, the conveyor belts 2a,b are at a distance b from one another that essentially corresponds to the target diameter or caliber of the sausage 3. In order to produce sausages having different calibers, and in order to be able to detect the form thereof, the conveyor belts can be moved towards and away from one another, as shown by the arrow K. The means of transport 2a,b are thereby moved in such a way that the midpoint M between the conveyor belts is always constant, in such a way that a sausage transported between the conveyor belts can always be guided with the center axis M of said sausage in the center, between the conveyor belts. Alternatively, only one means of transport may be moved, in which case the sensors are moved in the same direction around half the distance. The measuring point P thereby lies in a plane, which is at the same distance from each of the two means of transport. Multiple parameters can be advantageously determined with the help of the at least one distance meter, here, the two distance meters. At least one of the following parameters is preferably thereby determined: Portion length, sausage caliber, direction of curvature, size of curvature, split casing, presence of a separation point between successive sausages.

The method according to the present disclosure is described in greater detail below.

In the case of the method according to the present disclosure, the produced sausage is transported on a transport device $2a,b$, here, between two circulating conveyor belts $2a,b$, as is especially evident from FIGS. 2$a$ and 1. While the sausage or a string of sausages having a specific number of individual sausages is transported between the conveyor belts $2a,b$ in the direction of transport T, the at least one distance sensor $1a,b$, here the two distance sensors, scan the sausage surface of the respective sausage at the measuring point P, while the sausage moves past the respective distance sensors $1a,b$. The distance c between the sensor and the sausage 3 is thereby detected. At least one parameter that relates to the shape of the sausage can be determined on the basis of this measured distance or distances respectively. A signal S1, S2 is thereby passed to an evaluation device 4 from the at least one sensor, in this case the two sensors $1a,b$, as shown in FIG. 11. The evaluation device 4 then determines a corresponding parameter. In order to determine a parameter, an additional signal S3 may be passed to the evaluation device 4 from a device 7, for example a transducer of the means of transport, wherein the signals S3 corresponds to the speed of the transport device, for example. The determined parameter can then be compared to a target value or a range of target values, after which a signal S4, which is a function of the parameter or the comparison is output, said signal controlling a further processing device 8, which feeds the corresponding sausage to a further processing step corresponding to the parameter.

The length of a sausage may be detected as a parameter, for example. In principle, this can also be done using a single sensor. FIG. 3 shows the distance signal level as a function of the time or distance. If the start of a sausage moves past the distance sensor $1a$ (or $1b$), the measuring beam is reflected and the detected distance signal S1 rises (see rising signal edge F1). As long as the sausage surface is passing the sensor, the detected distance signal S1 retains a high level. Light is no longer reflected at the end of the sausage, so the detected distance signal S1 drops to zero (see falling signal edge F2). The length of the sausage can be determined from the rising and falling signal edge F1, F2 and the distance traveled between the rising and falling signal edge. The distance traveled can be determined by means of the number of increments of the drive on a means of transport.

A corresponding signal S3, by means of which the distance traveled can be determined, may be relayed by transducers of the conveyor belts 7 or by a control unit 5, for example in the form of the speed.

Figure 10:
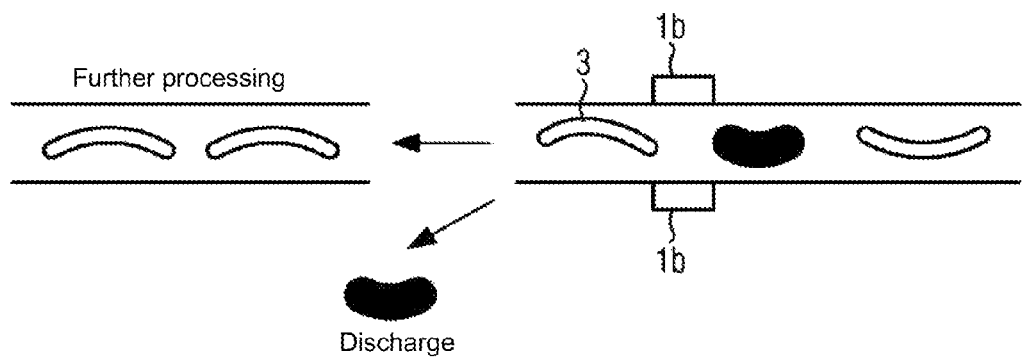
FIG. 10 shows a rough schematic representation of a cross section through the apparatus according to the disclosure, wherein a sausage is discharged.

If the portion length has been determined, the portion length will be compared in the comparison unit in evaluation device 4 to a corresponding target value or range of target values that were previously entered. If the length falls within the guideline including tolerances, it may be further processed, as is shown in FIG. 10, and fed to further processing steps. If the length does not fall within the corresponding range of target values, the corresponding sausage will be discharged. Sausages having different lengths may be further processed differently.

When the caliber is to be determined as a parameter, both sensors are needed. The two distance sensors are mounted at a defined distance a from one another on either side of the conveyor belts $2a,b$. The two measured distances c to the sausage are subtracted from the distance of the distance sensors $1a,b$ in order to thus determine the caliber (see FIG. 6).

Figure 6:
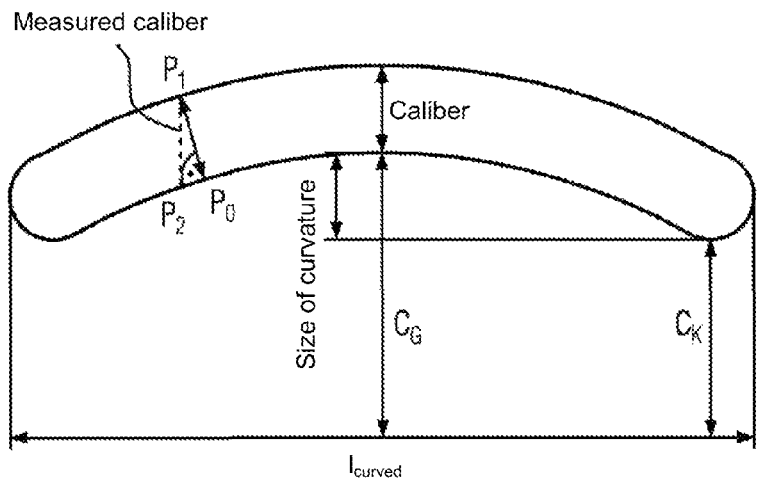
FIG. 6 shows a rough schematic representation of the size of curvature, the caliber and the length of the sausage.

The measured caliber in the center of a curved sausage corresponds to the actual caliber of the sausage. In the case of curved sausages, the measured caliber in the curved regions deviates from the actual caliber ab, as can be seen in FIG. 6. The actual caliber is the diameter essentially perpendicular to the tangent at a point on the curved sausage surface. The measured caliber can be corrected as a function of the determined curvature: In order to determine the actual caliber, i.e. in the case of curved sausages, the diameter perpendicular to a tangent at a specific point of the sausage can be calculated, for example by means of a trigonometric calculation. In order to determine the actual caliber, for example, a slope between two points can be determined, for example between the points P2 and P0 in FIG. 6. The measure of the actual caliber can then be calculated from the known distances $\overline{P1,P2}$ and $\overline{P2,P0}$. This calculation is simply an example of a possible correction.

By determining the caliber, it is possible to determine whether the casing is underfilled or overfilled. In so doing, the caliber of the sausage determined along the length is thereby compared to corresponding target values or ranges of target values respectively. If the length does not fall within the guideline including tolerances, it is discharged, as previously shown in conjunction with FIG. 10. Those sausages that fall within the tolerances can be further processed. Sausages having different lengths may be further processed differently.

Furthermore, the curvature can be detected as a parameter.

Figure 4:
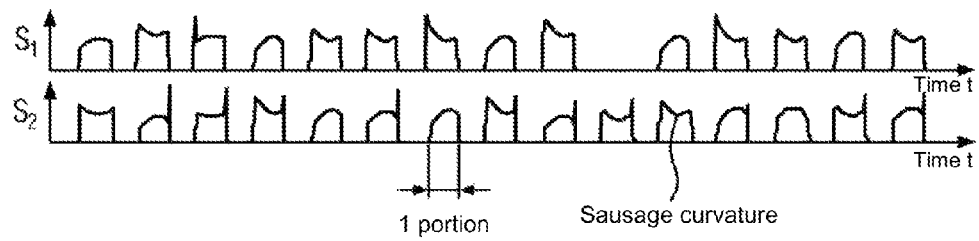
FIG. 4 shows a schematic representation of a distance signal as a function of the time for the recognition of the direction of curvature.

As can be seen FIG. 4, curved sausages have a distance signal, which is not constant between the rising and falling signal edge, but instead which is convex or concave. The convex or concave direction of curvature then reflects the direction of curvature of the respective sausage.

Figure 5:
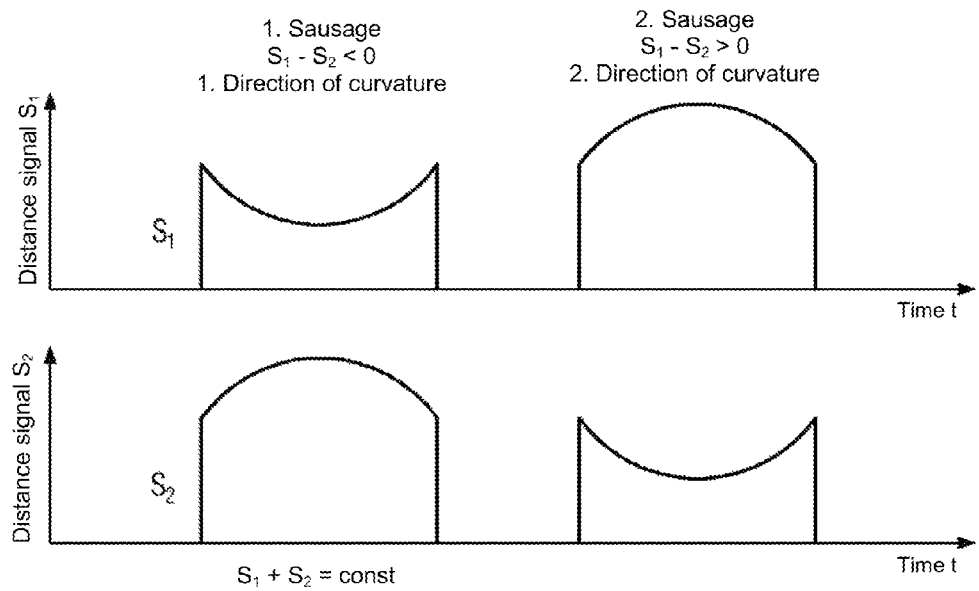
FIG. 5 shows a rough schematic representation of a section of the signal characteristic illustrated in FIG. 4.

The direction of curvature is especially easy to detect with the help of two sensors. In the case of curved sausages, the distance signal of the second distance sensor is always the reverse of the distance signal of the first sensor as long as the casing of the sausage has not burst. Partially occurring, unexpected signal peaks may be filtered out if necessary. As is especially evident from FIG. 5, one distance sensor $1a$ generates a distance sensor signal S1 for a first sausage, for example, wherein the signal level S1 first drops and then rises again between the rising and falling signal edge. The behavior of the signal level S2 of the opposite sensor is the reverse, such that $S_1+S_2$=Const. If one distance signal is now subtracted from the other distance signal, for example $S_1-S_2$, a value is obtained that is <0, which indicates a first direction of curvature, in this case, for example, to the left. In the case of a second sausage having a second direction of curvature, for example curved to the right, the result is $S_1-S_2>0$.

Figure 9:
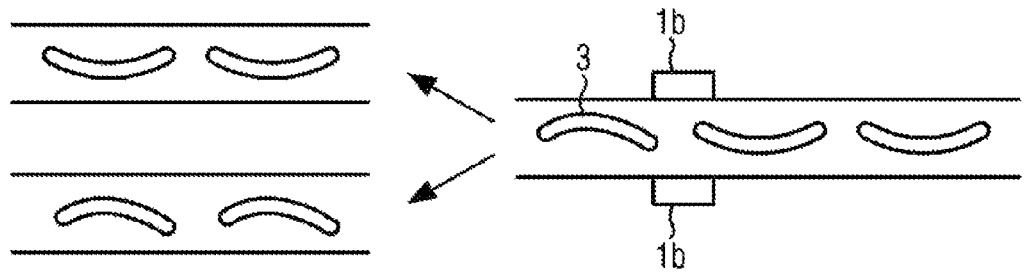
FIG. 9 shows a rough schematic representation of a cross section through the apparatus according to the disclosure, as well as various subsequent processing steps.

If the direction of curvature has been determined, it is possible to form a group of sausages having the same orientation, as shown for example in FIG. 9. Here, for example sausages having a first direction of curvature are passed to different transport device than sausages having a second curvature. Sausages having the same direction of curvature can then be placed precisely in the appropriate trays.

Thus the direction of curvature can be determined in a simple manner.

Furthermore, the size of curvature can be also determined as a parameter. As can be seen in FIG. 6, the size of curvature can be determined over the course of the distance signal level when a sausage passes through the measurement point P. In FIG. 6, the size of curvature is obtained by subtracting the smallest measured distance signal $C_K$ from the largest determined distance measure $C_G$.

By measuring the distances at two consecutive points, it is also possible to determine a corresponding slope in a specific region.

The actual extended length of the sausage can be calculated from the two measured values; "curved length" $l_{curved}$ (chord length) and the size of curvature.

According to the present disclosure, whether a separation point exists can also be determined as a parameter.

Figure 7:
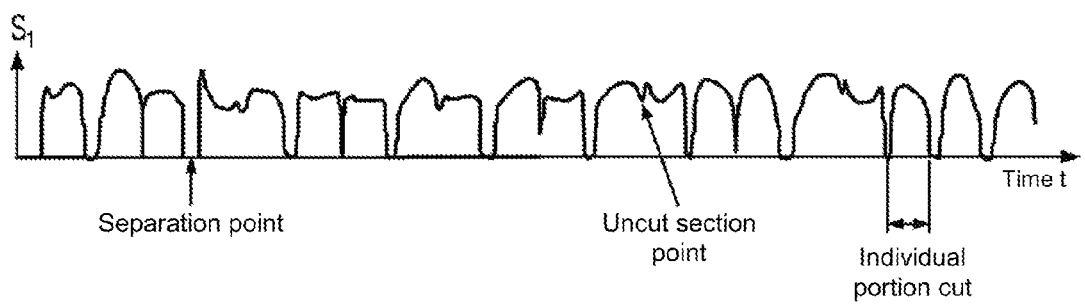
FIG. 7 shows a rough schematic representation of the height of the distance signal as a function of the time for determining, whether a separation point exists or not.

As can be seen in FIG. 7, a separation point between two consecutive sausages 3 exists when the distance signal falls to zero, since there is no reflection of the measurement beam. On the embodiment shown in FIG. 7, two sausages 3 are linked together in the front portion of the diagram, wherein there is a separation point after the second sausage, and the signal falls to zero over a specific period of time. Since the signal does not fall to zero between the two linked sausages, it is possible to determine that the sausages are linked. Thus cut, individual portions are shown at the end of the diagram, in which the signal falls to zero after each sausage. Thus it is possible to tightly control whether a separation point actually exists, or whether an error has occurred during separation. Sausages or strings of sausages that have not been correctly separated can this be discharged, for example, wherein the evaluation device determines "not properly separated" as a parameter and a signal S4 for discharging is generated.

It is also possible to determine whether a split casing exists as a parameter.

Figure 8:
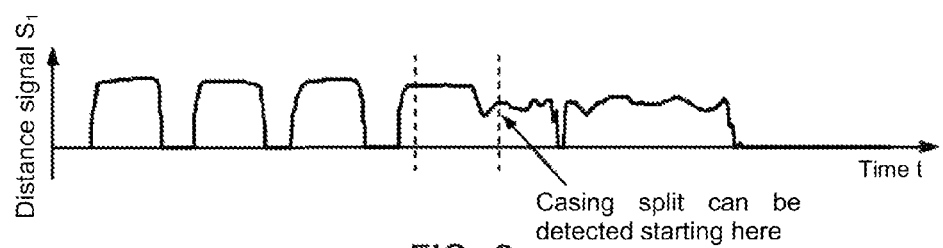
FIG. 8 shows a rough schematic representation of the height of the distance signal as a function of the time for the recognition of split casings.

As can be seen in FIG. 8, there is no falling signal edge after the fourth falling edge after a predetermined time interval, but instead, there is a fluctuating distance signal. Starting at the dashed line, it is possible to determine that a split casing exists. That means that a split casing exists when there is no falling signal edge after a specific period of time after a rising signal edge. The evaluation device 4 then determines a "split casing" as a parameter and generates a signal S4 to discharge the sausage in accordance with FIG. 10.

In the present disclosure, it is especially advantageous that with the help of one measuring arrangement, that is, with the help of at least one distance sensor, a plurality of parameters describing the shape of the sausage can be determined, and appropriate further processing steps can be initiated depending on these parameters.

Figure 12:
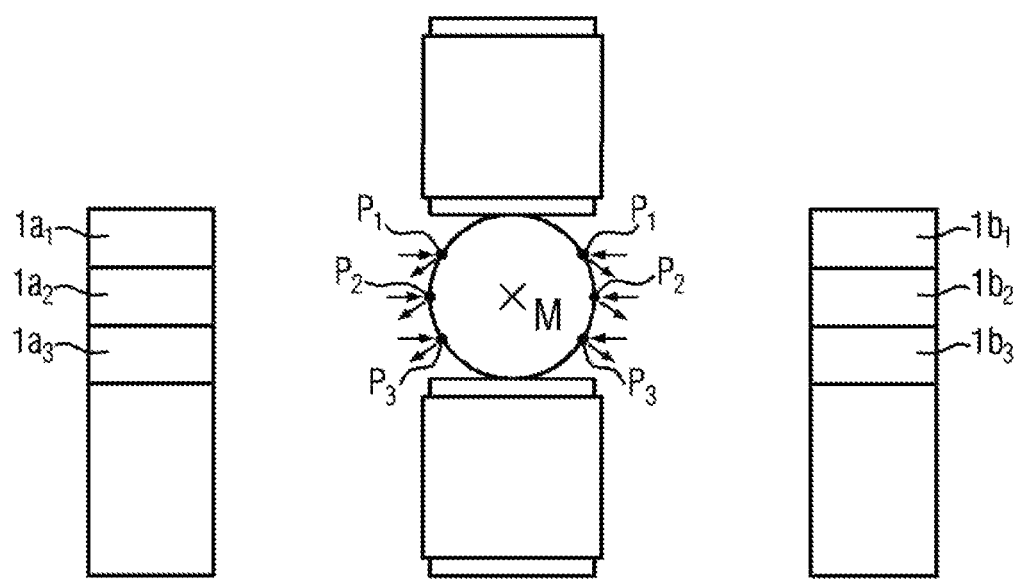
FIG. 12 shows a further possible embodiment according to the present disclosure having a plurality of distance sensors disposed one above the other.

FIG. 12 shows a further possible embodiment according to the present disclosure. The embodiment corresponds to the embodiment shown in FIG. 1, wherein here, however, a plurality of distance sensors $1a_b$, $1a_2$, $1a_3$, $1b_1$, $1b_2$, $1b_3$ are laterally disposed with respect to the transport device, disposed one above the other. In this way, a plurality of measuring points P1, P2, P3 can be detected on the surface of the sausage. Thus, for example, it is possible to ensure that a twist in the sausage casing which for example in the case of an intestinal casing, is not located completely centered between the sausages, can be detected by a sensor device. Alternatively to the embodiment shown in FIG. 12, in addition to the measuring device shown in FIG. 1, a line sensor may be perpendicularly disposed with respect to the direction of transport, laterally disposed beside the conveyor belts, said line sensor detecting the presence of a twist in the sausage casing in order to detect a separation point, which may not be located precisely in the middle M.

The invention claimed is:

1. An apparatus for determining at least one parameter relating to the shape of a sausage, which is transported on a transport device, comprising:
    a measuring device, which comprises at least one distance sensor disposed in such a way that said sensor can detect a distance (c) to a sausage that is being transported, and
    an evaluation device, which determines at least one parameter relating to the shape of the sausage as a function of the distance (c), wherein the evaluation device determines as said at least one parameter a direction of curvature of the sausage and/or a size of curvature of the sausage, and the evaluation device being designed in such a way that a signal (S4) is generated as a function of the at least one parameter, in order to transport the sausage for corresponding further processing steps.

2. The apparatus according to claim 1, in which at least one of the following parameters is determined:
    portion length, caliber, split casing, presence of a separation point between successive sausage portions.

3. The apparatus according to claim 1, wherein the at least one distance sensor is a reflex scanner.

4. The apparatus of claim 3, the distance sensor including one of a laser distance sensor or an infrared sensor.

5. The apparatus according to claim 1, the measuring device comprising two distance sensors, which are disposed on opposite sides of the transport device at defined locations.

6. The apparatus according to claim 1, the measuring device having a plurality of distance sensors ($1a_1$, $1b_2$, $1a_3$, $1b_1$, $1b_2$, $1b_3$), which are disposed one above the other in a direction that extends perpendicular to a transport direction (T) of the sausages.

7. The apparatus of claim 1, the transport device including two circulating means of transport.

8. The apparatus according to claim 7, the at least one distance sensor being disposed at a height, in such a way that a measuring point (P) lies on a plane, which is at the same distance from each of the two circulating means of transport.

9. The apparatus according to claim 7, the distance (b) of both circulating means of transport relative to one another is adjustable, in such a way that the midpoint (M) between the means of transport remains constant.

10. The apparatus of claim 7, the measuring device comprising two distance sensors which are disposed on opposite sides of the two circulating means of transport.

11. The apparatus according to claim 1, in which a line sensor is provided, the line sensor disposed perpendicular to the transport device.

12. A method for determining at least one parameter relating to the shape of the sausage, comprising:
    transporting a produced sausage on a transport device;
    detecting, while transporting the produced sausage, a distance (c) from a defined location to the produced sausage; and
    determining as a parameter a direction of curvature of the produced sausage and/or a size of curvature of the produced sausage as a function of the detected distance (c),
    wherein a signal (S4) is generated as a function of the parameter by an evaluation device, in order to transport the sausage for corresponding further processing steps.

13. The method according to claim 12, and measuring the distance (c) from two sides that are opposite one another with respect to the transport device, and determining the at least one parameter as a function of the two distances.

14. The method according to claim 12, further comprising:
comparing the at least one determined parameter to a target parameter or range of target parameters.

15. The method according to claim 12, wherein detecting the distance (c) comprises determining said distance (c) as one of a function of the time or a distance traveled by the transport device.

16. The method according to claim 12, further comprising calculating the length of the sausage as a parameter from a rising and falling signal edge (F1, F2) of a distance signal (S1, S2), and the distance therebetween traveled by the transport device.

17. The method according to claim 16, further comprising determining a parameter of a direction of curvature of the produced sausage by detecting a direction of curvature of the distance signal characteristic (S1, S2).

18. The method according to claim 16, further comprising, determining the distance as a function of one of the time or the distance on opposite sides of the transport device, the distance signal characteristic on the opposite sides being reversed, and calculating the direction of curvature from opposing distance signals (S1, S2).

19. The method according to claim 12, and further comprising:
determining a sausage caliber of the produced sausage as a parameter;
measuring the distance (c) to the sausage from two distance sensors disposed opposite one another at defined locations; and
subtracting the two measured distances in order to determine the caliber from the distance (a) of the sensors.

20. The method according to claim 12, and obtaining the size of curvature by subtracting a smallest measured distance signal from a largest measured distance signal.

21. The method according to claim 19, and with curved sausages, correcting the determined caliber as a function of sausage curvature.

22. The method according to claim 12, and determining whether a separation point between successive sausages exists, when a distance signal drops to zero or falls below a specific threshold value for one of a predetermined period of time or a predetermined transport distance.

23. The method according to claim 12, and determining an the existence of a split casing by identifying when no sinking signal edge occurs after a rising signal edge after a specific period of time.

24. The method according to claim 12, further comprising:
forming groups of sausages having the same direction of curvature; and
at least one of
transporting the groups of sausages on different, further transport devices depending on the direction of curvature, or
placing the group of sausages in different receptacles.

* * * * *